(12) United States Patent
Delbeke et al.

(10) Patent No.: US 10,105,081 B2
(45) Date of Patent: *Oct. 23, 2018

(54) IMPLANTABLE SENSOR

(71) Applicant: INDIGO DIABETES NV, Ghent (BE)

(72) Inventors: Danae Delbeke, Gentbrugge (BE); Roeland Baets, Deinze (BE); Wim Bogaerts, Melle (BE); Eva Maria Paula Ryckeboer, Ghent (BE)

(73) Assignee: INDIGO DIABETES NV, Ghent (BE)

( * ) Notice: Subject to any disclaimer, the term of this patent is extended or adjusted under 35 U.S.C. 154(b) by 151 days.

This patent is subject to a terminal disclaimer.

(21) Appl. No.: 15/358,917

(22) Filed: Nov. 22, 2016

(65) Prior Publication Data

US 2017/0071510 A1 Mar. 16, 2017

Related U.S. Application Data

(63) Continuation-in-part of application No. 13/415,392, filed on Mar. 8, 2012, now Pat. No. 9,532,738, which
(Continued)

(30) Foreign Application Priority Data

Sep. 9, 2010 (GB) .................................. 0915775.1

(51) Int. Cl.
*A61B 5/1455* (2006.01)
*A61B 5/145* (2006.01)
(Continued)

(52) U.S. Cl.
CPC .......... *A61B 5/1455* (2013.01); *A61B 5/0031* (2013.01); *A61B 5/1459* (2013.01);
(Continued)

(58) Field of Classification Search
CPC ... A61B 5/0031; A61B 5/0059; A61B 5/0066; A61B 5/0075; A61B 5/145;
(Continued)

(56) References Cited

U.S. PATENT DOCUMENTS

| 4,344,438 A | 8/1982 | Schultz |
| 5,267,151 A | 11/1993 | Ham et al. |

(Continued)

FOREIGN PATENT DOCUMENTS

| DE | 10 2009 010 955 A1 | 9/2010 |
| EP | 1353200 A2 | 10/2003 |
| WO | 2009 156410 A1 | 12/2009 |

OTHER PUBLICATIONS

Fard, Sahba Talebi, et al., "Optical Absorption Glucose Measurements Using 2.3-μm Vertical-Cavity Semiconductor Lasers", IEEE Photonics Technology Letters, vol. 20, No. 11, Jun. 1, 2008, pp. 930-932.

(Continued)

*Primary Examiner* — Eric Winakur
*Assistant Examiner* — Chu Chuan (JJ) Liu
(74) *Attorney, Agent, or Firm* — Bacon & Thomas, PLLC

(57) ABSTRACT

A sensor for sensing a substance such as for example glucose. The sensor is implantable in the body of a living creature. The sensor has a photonic integrated circuit, e.g. silicon-photonics integrated circuit, for spectrally processing radiation interacting with the sample. A continuous monitoring system can also include such a sensor.

20 Claims, 9 Drawing Sheets

Related U.S. Application Data is a continuation-in-part of application No. PCT/EP2010/063263, filed on Sep. 9, 2010.

(51) Int. Cl.
  *A61B 5/1459* (2006.01)
  *A61B 5/00* (2006.01)
  *G02B 6/12* (2006.01)
  *G02B 6/34* (2006.01)

(52) U.S. Cl.
  CPC ...... *A61B 5/14532* (2013.01); *A61B 5/14546* (2013.01); *A61B 5/0066* (2013.01); *A61B 2562/028* (2013.01); *G02B 6/12021* (2013.01); *G02B 6/34* (2013.01); *G02B 2006/12061* (2013.01); *G02B 2006/12107* (2013.01); *G02B 2006/12123* (2013.01); *G02B 2006/12138* (2013.01)

(58) Field of Classification Search
  CPC ............ A61B 5/24503; A61B 5/14507; A61B 5/1451; A61B 5/14532; A61B 5/14546; A61B 5/14551; A61B 5/14552; A61B 5/1459
  See application file for complete search history.

(56) References Cited

U.S. PATENT DOCUMENTS

| | | |
|---|---|---|
| 5,297,548 A | 3/1994 | Pologe |
| 5,348,003 A | 9/1994 | Caro |
| 5,722,397 A | 3/1998 | Eppstein |
| 5,833,603 A | 11/1998 | Kovacs et al. |
| 5,945,343 A | 8/1999 | Munkholm |
| 6,304,766 B1 | 10/2001 | Colvin, Jr. |
| 6,997,879 B1 | 2/2006 | Turcott |
| 7,236,812 B1 | 6/2007 | Ballerstadt et al. |
| 2002/0085784 A1 | 7/2002 | Reimer |
| 2003/0209669 A1 | 11/2003 | Chou |
| 2004/0162470 A1 | 8/2004 | Tu |
| 2004/0186359 A1 | 9/2004 | Beaudoin et al. |
| 2005/0047702 A1 | 3/2005 | Parker et al. |
| 2007/0066877 A1 | 3/2007 | Arnold et al. |
| 2008/0186483 A1 | 8/2008 | Kiesel et al. |
| 2010/0171028 A1 | 7/2010 | Wong et al. |

OTHER PUBLICATIONS

Luo et al, "An Integrated Photonic Sensor for in Situ Monitoring of Hazardous Organics", Sensors and Actuators B, Elsevier sequoia S.A., Lausanne, CH., vol. 92, No. 1-2, Jul. 1, 2003, pp. 121-126.

Katrien De Vos et al. "Label-Free Biosensors on Silicon-on-Insulator Optical Chips Based on Microring Cavities and Surface Plasmon Interferometry", Transparent Optical Networks, 2008. Jun. 22, 2008, pp. 88-91.

International Search Report dated Jan. 27, 2011 in PCT/EP2010/063263.

European Office Action dated Feb. 23, 2015, for EP 10 760 633.7.

IMPLANTABLE SENSOR

CROSS REFERENCE

This application is a continuation-in-part application claiming benefit of U.S. patent application Ser. No. 13/415,392, filed Mar. 8, 2012, which is a continuation-in-part application claiming the benefit of international application PCT/EP2010/063263, filed Sep. 9, 2010, which claims the benefit of British application GB 0915775.1, filed Sep. 9, 2009, the entirety of said applications being incorporated herein by reference.

FIELD

The invention relates to the field of implantable sensors. More particularly, the present invention relates to implantable sensors for sensing substances and to corresponding continuous monitoring systems.

BACKGROUND OF THE INVENTION

According to the estimates of the World Health Organization (WHO), the number of people with diabetes will increase from 177 million in 2000 to 300 million by 2025. It is also estimated that 9% of all deaths worldwide are due to diabetes. Although diabetes is presently not curable, intensive insulin therapy in diabetic patients can dramatically delay the onset of serious complications.

The cornerstone to tight glycemic control is frequent or even continuous glucose monitoring, where blood glucose concentrations are measured to help administer proper levels of insulin and maintain euglycemic conditions. Continuous glucose monitoring (in practice a measurement every few minutes) is the prerequisite to enable strict glycemic control lowering the blood glucose levels within a "healthy" range (80-110 mg/dl) that prevents medical complications while avoiding dangerously low blood glucose concentrations (hypoglycemia). The ability to maintain blood glucose levels within this healthy range requires frequent measurements of glucose concentrations in the blood. Each measurement provides information that can be used to deliver the proper amount and type of insulin to maintain blood glucose levels within the targeted concentration range.

It is demonstrated that tight or continuous blood glucose control can introduce substantial reductions in overall medical care costs. Glucose sensing technology has advanced considerably in recent years, thereby providing excellent tools for home glucose monitoring and establishing opportunities for tight glycemic control. Unfortunately, the cost and pain associated with current glucose test-strip technology generally restrict the number of daily measurements performed by the average person with diabetes (on average 4-6 times a day).

Examples of next-generation sensors are implantable glucose bio-sensors. To date, implantable glucose sensors are all based on surface chemical reactions. Such sensors are very stable, accurate and sensitive in vitro. However, once the sensors are implanted, the stability and reliability reduces dramatically after a few days owing in large part to fouling of the sensor surface by proteinaceous material. They can therefore not be used for long term implantation. Alternative sensors under study are based on spectrometric devices which should allow long term in vivo operation thus justifying the surgical procedure to implant the device.

Some initiatives in the domain of subcutaneously implantable spectroscopic sensors are already reported. In US2007/0066877 A1, an implantable sensor device is established. In vitro testing confirms practicability of the invasive concept and the feasibility of target specifications. The device has a fluid inlet port, a measurement volume and a fluid outlet port. Bodily fluid and/or target analyte is forced to the measurement volume using micro-dialysis or ultra-filtration with vacuum source and analysed using a spectrometer. In "Optical Absorption Glucose Measurements Using 2.3-µm Vertical-Cavity Semiconductor Lasers" IEEE phot. Tech. lett., 20(11), pp. 930-933, 2008, the development of a 2.3 µm vertical-cavity semiconductor laser (VCSEL) is reported for applications wherein the tunable VCSEL and detector are packaged as an implantable design. However the finite tuning range of 5 nm that can be reached with the VCSEL limits the potential for in vivo use of the radiation source.

SUMMARY OF THE INVENTION

It is an object of embodiments of the present invention to provide good implantable sensors for sensing substances as well as corresponding monitoring systems. Sensing substances may include detecting or identifying targets of interest, but also may include sensing a sample for imaging it.

It is an advantage of embodiments according to the present invention that an implantable single-chip optical sensor for continuous monitoring, e.g. continuous glucose monitoring (CGM) is provided. It is an advantage of embodiments according to the present invention that the sensor can be made small, resulting in good implantation properties. It is an advantage of embodiments according to the present invention that a reagent-free, optical analysis method can be used, so that no direct contact between the sensor and the object (e.g. fluid or tissue) to be measured is required. It is an advantage of embodiments according to the present invention that the sensor can be made small, allowing optically good biocompatible packaging. The shape of the sensor may allow small thickness of the biocompatible packaging, so that absorption and diffraction by the packaging can be limited. The sensor may be substantially flat. Good biocompatible packaging may reduce or minimize bio-fouling. Furthermore, being an optical analysis method, a reduced or minimized bio-fouling might be less harmful, as the small bio-fouling results in substantial optical transparency, in contrary to biosensors for which minimal fouling often obstructs their activity.

It is an advantage of embodiments of the present invention that advanced optical processor may be provided in the sensor, allowing advanced and optionally complex radiation processing, e.g. allowing spectral and depth-resolved processing of radiation received or guided to a measurement region.

It is an advantage of embodiments according to the present invention that systems can be made such that there is no need for a stimulated flow or stimulated diffusion or stimulated displacement of material to enable sensing, i.e. that the sample or substance transport to the measurement region can be based on natural or spontaneous displacement. In this way, an extraction means for extracting fluid, a micro-cannula, a microdialysis probe, an ultrafiltration probe, etc. to extract material to a sample region can be avoided, resulting in significant advantages regarding amongst others ease of implantation and patient comfort, mechanical stability, reliability and need for powering. The latter is obtainable due to the miniaturisation of the sensor used, e.g. due to the miniaturisation of an optical processor as photonic integrated circuit.

It is an advantage of embodiments according to the present invention that the sensor has substantially direct access to the substance or sample under study.

It is an advantage of embodiments according to the present invention that it can assist in providing a closed-loop drug delivery system, such as a closed-loop insulin delivery system that is implantable within a patient's body. Sensors according to embodiments of the present invention therefore may be coupled to a drug delivery system.

It is an advantage of embodiments according to the present invention that it can assist in non-invasive—after implantation—measurements e.g. glucose or urea measurements, allowing high frequency tests without patient discomfort.

It is an advantage of embodiments according to the present invention that substance sensing, e.g. glucose, urea, cotinine, triglyceride, protein, cholesterol, ethanol, ketones, hormones or lactate sensing, can be performed in a disposable free manner, resulting in a reduced cost.

The above objective is accomplished by a method and device according to the present invention.

The present invention relates to a sensor for sensing a substance, the sensor being implantable in the body of a living creature or an object and configured for sensing in tissue or bodily fluids, and the sensor comprising an integrated radiation source configured for coupling radiation generated by said source into a photonics integrated circuit, the integrated radiation source being for irradiating said tissue or bodily fluids having at least one of glucose, urea, creatinine, triglyceride, protein, cholesterol, ethanol, ketones, hormones or lactate in said tissue or bodily fluid a photonics integrated circuit configured to spectrally process the radiation interacting with the glucose, urea, creatinine, triglyceride, protein, cholesterol, ethanol, ketones, hormones or lactate, wherein the photonics integrated circuit comprises at least an integrated optical waveguide, an optical demultiplexer and a detection element, said integrated optical waveguide being configured for receiving radiation from said integrated radiation source and to send the radiation to the demultiplexer, said optical de-multiplexer being configured for spectrally processing the radiation, said integrated detection element being configured to detect different absorption or reflection bands of the glucose, urea, creatinine, triglyceride, protein, cholesterol, ethanol, ketones, hormones or lactate from the spectrally processed radiation to sense the glucose, urea, creatinine, triglyceride, protein, cholesterol, ethanol, ketones, hormones or lactate, wherein the radiation source and the silicon photonics integrated circuit form an integrated spectrometer, and wherein said sensor is configured to be implantable in the body of a living creature or an object to sense glucose, urea, creatinine, triglyceride, protein, cholesterol, ethanol, ketones, hormones or lactate is an advantage of embodiments according to the present invention that accurate and reliable sensors can be provided that are implantable and usable for long term continuous monitoring applications, without the need for user intervention.

The photonics integrated circuit may be a silicon photonics integrated circuit.

The photonics integrated circuit may comprise at least one multiplexer and/or one de-multiplexer. The multiplexer and/or demultiplexer may allow combining and/or splitting spectrally resolved information, e.g. obtained from the spectrally processed radiation.

The sensor may be waveguide based and may be configured for evanescent sensing. Alternatively, the sensor may be waveguide based and may be configured for free space sensing.

The photonics integrated circuit may comprise at least one multiplexer and/or one demultiplexer and the sensor may be waveguide based and configured for evanescent sensing of free space sensing.

The sensor may comprise a measurement region from which the radiation is captured, the photonics integrated circuit and measurement region being adapted to allow for substance-sampling free measurements. In other words, in embodiments of the present invention, no extraction or probing must be performed.

The sensor may comprise a measurement region from which radiation is captured, the radiation processor and measurement region being adapted in size so as to allow for time-dependent substance measurements based on spontaneous displacement of the substance in the body. It is an advantage of embodiments according to the present invention that using a photonics integrated circuit based sensor, the sensor can be adapted in size such that time dependent measurements of the sample can be performed based on the natural flow of sample through the body of the living creature, without the need for a forced flow or displacement using a sampling means such as for example a pumping system such as a mechanical or electromechanical pump system, a fluid extractor, a micro-cannula, a micro dialysis probe, an ultra-filtration probe, an implanted wick. It is an advantage of embodiments according to the present invention that more reliable and robust sensors can be obtained, with less or no mechanically moving components such as pumps.

The measurement region may be an open-space measurement region so that it is not substantially enclosed by sensor walls. The number of mechanical sensor walls around the measurement region may be less than 2, e.g. only at one side a sensor wall may be present. The measurement region therefore may not be a closed room with an inlet and/or outlet.

It is an advantage of embodiments according to the present invention that the photonics integrated circuit, e.g. silicon-photonics integrated circuit, based sensor can inherently be small so that only a small sample chamber of measurement region is required, resulting in smaller sample volumes being measurable. The latter can assists in continuous flow measurements because it allows on the one hand to use natural flow of the sample in the body and on the other hand provides more detailed results as smaller volumes can be probed.

The sensor may comprise a photonic-integrated-circuit-compatible, integrated detecting element for detecting radiation processed in the photonics integrated circuit. It is an advantage of embodiments according to the present invention that integration of the sensor may result in a small footprint of the sensor.

The detecting element may be a detecting element monolithically integrated with the photonics integrated circuit or a heterogeneously integrated with the photonics integrated circuit or a hybridly integrated with the photonics integrated circuit. It is an advantage of embodiments according to the present invention that monolithic integration or heterogeneous integration or hybrid integration may result in an easy manufacturing. The detecting element may be fibre-coupled to the photonics integrated circuit.

The sensor may comprise a photonics integrated circuit compatible, integrated radiation source for irradiating a substance or a sample comprising the substance in a measurement region.

The radiation source may be a radiation source monolithically integrated with photonics integrated circuit or heterogeneously integrated with the photonics integrated circuit or hybridly integrated with the photonics integrated circuit.

The radiation source may be fibre-coupled to the photonics integrated circuit.

The photonics integrated circuit based sensor may optionally be adapted for operating in at least a wavelength region of 1560 nm to 1850 nm and/or is adapted for operating in at least a wavelength region of 2080 nm to 2325 nm.

The photonics integrated circuit may comprise a spectrometer for obtaining spectrally resolved information from the spectrally processed radiation after interaction. According to embodiments of the present invention, detecting spectral information regarding the absorption or scattering may allow for accurate detection of absorption bands of e.g. glucose. It is an advantage of embodiments according to the present invention that spectrally resolved information can be obtained as this allows for more accurate detection of glucose due to the possibility of detecting different absorption or reflection bands of glucose in the sample.

The sensor may have a sensor configuration such that a measurement region of the sensor is surrounded by components of the sensor. It is an advantage of some embodiments according to the present invention that transmission measurements, reflection measurements, absorption measurements as well as scattering measurements may be performed.

The sensor may have a sensor configuration such that a measurement region of the sensor lies substantially at one side of all components of the sensor. It is an advantage of embodiments according to the present invention that the measurement region may not be provided as channels, therefore being less prone to obstruction. The sensor configuration may be adapted for obtaining depth-related information regarding the sample. It is an advantage of embodiments according to the present invention that depth related sample information can be obtained, as the latter allows taking into account separation of the sample from the sensor through other tissue, such as for example collagen deposits. The sensor configuration may be configured as an optical coherence tomography sensor. The sensor configuration may be configured as a spectrally resolved optical coherence tomography sensor and wherein the radiation processor may comprise an interferometer and may be adapted for processing obtained interference data in several different windows. It is an advantage of embodiments according to the present invention that both spectrally and depth resolved measurements can be performed, allowing more accurate detection of a substance in the sample.

The sensor configuration may be configured for spatially resolved detection and for deriving said depth-resolved information regarding the sample based thereon.

The photonics integrated circuit may be adapted for spatially resolved detection of scattered or reflected radiation.

The radiation processor may comprise a plurality of cascading wavelength multiplexers or demultiplexers for increasing a number of channels for spectrally processing radiation.

The photonics integrated circuit may comprise a plurality of tunable filters or filters for increasing a number of channels for spectrally processing radiation.

Frequency or time-domain multiplexing may be used for increasing a number of channels for spectrally processing radiation.

A Vernier-shifted spectral response may be used for increasing a number of channels for spectrally processing radiation.

The sensor may comprise an electronics component stacked with the sensing element and radiation source, wherein the connection between sensing element and radiation source on the one hand and the electronics on the other hand is made by through silicon vias.

The sensor may be adapted for sensing any of glucose, urea, creatinine triglyceride, protein cholesterol, ethanol, ketones, hormone or lactate.

The sensor may be adapted for imaging the substance by optical coherence tomography.

The sensor may be implantable in a bioreactor.

The sensor may be provided with bodily fluid extraction means or radiation guiding means for extracting bodily fluid from the body or for guiding radiation to and from the sample, other components of the sensor being configured for extra-vivo use rather than being implantable.

The present invention also relates to a continuous monitoring system comprising an implantable sensor for sensing a substance as described above and a readout system for wirelessly receiving data sensed by the sensor.

The present invention also relates to the use of an implantable sensor as describe above as glucose sensor. Such use may be for sensing a glucose level in the body of a living creature.

The present invention also relates to the use of an implantable sensor as describe above as urea sensor. Such use may be for sensing a urea level in the body of a living creature.

The present invention also relates to the use of an implantable sensor as describe above as creatinine, triglyceride, protein, cholesterol, ethanol, ketones, hormones or lactate sensor.

In some embodiments, the present invention also relates to a method for sensing a substance, the method comprising receiving radiation interacting with a sample, prior or after said interacting, spectrally processing the radiation using a photonics integrated circuit based radiation processor. The method optionally further may comprise method steps corresponding with the functionality of the different components described for the sensor above.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

Figure 1:
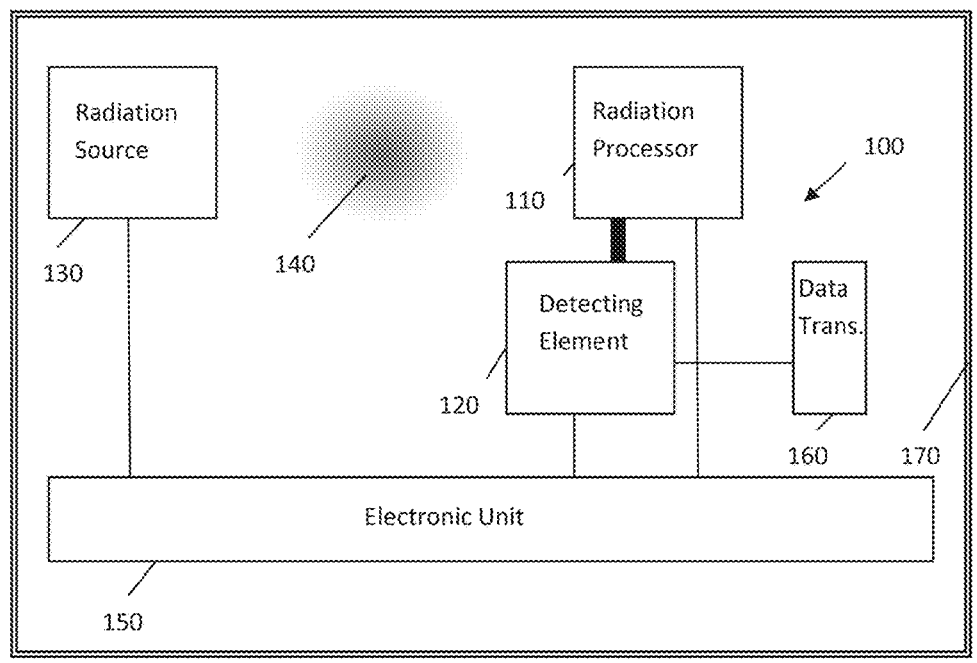
FIG. 1 illustrates a schematic example of components of a sensor according to an embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF THE INVENTION

Where in embodiments of the present application reference is made to a photonics integrated circuit (PIC), this refers to a variety of forms and material systems such as for example low-index contrast waveguide platforms (e.g. polymer waveguides, glass/silica waveguides, $Al_xGa_{1-x}As$ waveguides, $In_xGa_{1-x}As_yP_{1-y}$ waveguides), high-index contrast waveguides (e.g. Silicon-on-Insulator, semiconductor membranes), plasmonic waveguides (e.g. metal nano-particle arrays, metal layers), also called Photonic Lightwave circuits (PLC). A photonic integrated circuit comprises at least one integrated optical component, such as for example but not limiting to an integrated optical cavity, an integrated optical resonator, an integrated optical interferometer, an integrated optical coupler, a waveguide, a taper, a tunable filter, a phase-shifter, a grating, a modulator, a detector, a source, a multiplexer, a demultiplexer or a combination thereof. The optical components can be active or passive. The components can be integrated for example monolithically, heterogeneously or hybridly. Monolithical integration is the integration technology that uses a single processing flow to process the diverse components potentially using different materials, e.g. integrated germanium detectors in silicon photonics IC. Heterogeneous integration is the integration technology for which the components are processed in separate process flows, which are then integrated at die or wafer level, e.g. BCB bonding, wafer bonding, and other bonding schemes, 3D integration. Hybrid integration is the integration of components or materials on processed photonic integrated platforms, e.g. flip-chipping of detectors, bumping, gluing, wire bonding, co-packaging, etc.

The devices and methods of the present invention are further described for the particular case of an SOI (Silicon-on-Insulator) material system, also referred to as silicon photonics system. However, the devices and methods of the present invention can be based on other material systems, such as for example III-V material systems, metallic layers, low index contrast material systems or a combination thereof.

Silicon-on-Insulator is a very interesting material system for highly integrated photonic circuits. The high refractive index contrast allows photonic waveguides and waveguide components with submicron dimensions to guide, bend and control light on a very small scale so that various functions can be integrated on a chip. Moreover SOI offers a flexible platform for integration with surface plasmon based components which in turn allows for even higher levels of miniaturization. Both waveguide types allow a high level of miniaturization, which is advantageous. Furthermore for both waveguide types light can be efficiently coupled in and out the PIC by use of e.g. a grating coupler or another coupling element.

Using Silicon-on-insulator also has some technological advantages. Due to the CMOS industry, silicon technology has reached a level of maturity that outperforms any other plane chip manufacturing technique by several orders of magnitude in terms of performance, reproducibility and throughput. Nano-photonic ICs can be fabricated with wafer scale-processes, which means that a wafer can contain a high amount of photonic integrated circuits. Combined with the commercial availability of large wafers at a relative moderate cost, this means that the price per photonic integrated circuit can be very low.

Where in the present application reference is made to "photonics integrated circuit compatible", reference is made to components that can be integrated in the semiconductor chip or platform.

Embodiments of the present invention typically may be used in pre-dispersive or post-dispersive applications. Where embodiments of the present invention refer to pre-dispersive applications, reference is made to embodiments wherein the radiation before interaction with the object to be measured is spectrally resolved. Where embodiments of the present invention refer to post-dispersive applications, reference is made to embodiments wherein the radiation after interaction with the object to be measured is split into individual components of different wavelengths. Where in embodiments of the present application reference is made to integration, such integration may comprise monolithical, heterogeneous or hybrid integration. In some embodiments, such integration also may enclose fibre coupling of components to the silicon chip or platform.

Where in embodiments of the present application reference is made to radiation, reference is made to electromagnetic radiation. The radiation envisaged is radiation having a suitable wavelength or wavelength range for sensing, i.e. detecting or imaging, a substance. In some embodiments radiation used will be infrared radiation, e.g. near infrared radiation or mid infrared radiation. In some embodiments, the radiation has a wavelength or wavelength range between 1200 nm and 2500 nm, or between 2500 nm and 10000 nm, or a combination thereof, although the invention is not limited thereto.

Where in embodiments of the present application reference is made to subcutaneous there is meant "under the skin". Where in embodiments of the present invention reference is made to intramuscular there is meant "inside a muscle". Where in embodiments of the present invention reference is made to retroperitoneal, reference is made to "in the abdominal cavity". Where in embodiments of the present invention reference is made to intravascular, reference is made to "inside a blood vessel", and whereby in embodiments of the present invention reference is made to extra-vascular, reference is made to "close vicinity to a blood vessel".

Where in embodiments reference is made to "interstitial", there is meant relating to or situated in the small narrow spaces between tissues or parts of an organ. Interstitial fluid is extracellular fluid that is present throughout the body and skin. It typically may be found in the outermost layers of the skin. Where in embodiments reference is made to tissue, the latter includes an aggregate of cells of a particular kind, together with their intercellular substance, that forms structural material. The substance of interest may be a target analyte being present in any sample such as for example in tissue, bodily fluid such as interstitial fluid, urine or blood, etc. Alternatively or in addition thereto, the substance also may be a tissue itself, whereby sensing may be performed for obtaining an image thereof.

In a first aspect, the present invention relates to a sensor for sensing a substance. Embodiments of the present invention are sensors for the sensing of a substance in the body of living creatures including the human being, but the invention is not limited thereto. The substance may be for example any of glucose, urea, creatinine, triglyceride, protein, cholesterol, ethanol, ketones, hormones or lactate. The living creature may be any organism for which a sample containing a target substance can be obtained. The living creature may be any creature wherein the sensor can be implanted. It may for example be a plant or an animal, such as a mammal or non-mammal. It may be cold-blooded or warm-blooded. In some preferred embodiments, sensors are provided for sensing glucose, although also sensors are provided for sensing of other substances, such as for example urea, lactate, creatinine, triglyceride, protein, cholesterol, ethanol, ketones, hormones or lactate; etc. Alternatively or in addition thereto, the substance thus also may include tissue itself and sensing may be performed for imaging purposes, e.g. blood vessels, nerves, cancer tissue, cellular changes, etc. It is to be noticed that the wavelength at which sensing is performed mainly may be determined by the substance to be sensed. The selection of a different substance to be sensed, i.e. detected, imaged or monitored, thus may result in the need for using similar components as described for glucose, but having operability in another wavelength region or converters therefore. For the sake of convenience, embodiments of the present invention will be further described with reference to glucose sensing, but it will be clear to the person skilled in the art that the description in the embodiments and examples is mutates mutandis applicable to embodiments of substance sensing in a different wavelength.

The sensor may be adapted—e.g. by a particular detecting element and/or radiation source as well as by optical components used in the optical processor- to be used in a the near infrared radiation wavelength range, e.g. in a range between 1200 nm and 2500 nm. The sensor may be adapted for use in those wavelength regions where glucose has particular absorption or scattering. For example, the sensor may be adapted for operating in the first-overtone band (1560 nm to 1850 nm) and/or the combination band (2080 nm to 2325 nm) where glucose has numerous absorption bands and water has relative lower absorption. The selection of which wavelength range used could for example be based on the available radiation sources and detectors and on the degree of absorption of glucose occurring. For the different embodiments, especially if the combination wavelength range is used, optimization may be performed such that minimal propagation losses are obtained while maintaining a single-mode condition over the entire wavelength range of interest.

A sensor according to embodiments of the present invention is implantable in the body of a living creature. More particularly, the sensor according to embodiments of the present invention may be implantable in the human body, but the invention is not limited thereto. The sensor may be for example implanted subcutaneous, intramuscular, retroperitoneal, extra-vascular, intravascular, ocular, vesicular, or implanted in an organ. Subcutaneous and intramuscular implants may happen at different locations, e.g. in the fore arm, the upper, arm, the abdomen, etc. According to embodiments of the present invention, the sensor comprises a photonic integrated circuit for spectrally processing radiation used for sensing a substance. Where in embodiments of the present invention reference is made to spectrally processing radiation, reference is made to processing of the radiation that influences the spectral behaviour of the radiation, such as for example splitting of different wavelength components into different radiation sub-beams, merging of beams having a different spectral composition into a single beam. In other words the sensor may be adapted for capturing radiation that was directed to a sample and that has interacted therewith and processing that radiation, for processing radiation that is then directed to a sample and interacts therewith or for a combination thereof. It is an advantage of embodiments according to the present invention that photonics integrated circuits are used allowing miniaturization of the sensor. It is an advantage of embodiments according to the present invention that sensing, i.e. detecting or imaging, can be performed without substance-sampling, i.e. without the need for extracting sample or guiding the substance of interest, e.g. incorporated in the sample, in a forced manner to a measurement region. In this way, there is thus no longer need to actively induce a displacement of substance by stimulated flow, stimulated diffusion, etc. such as for example using micro-dialysis, micro-cannula, ultra-filtration or another sampling probe or extraction means. It is an advantage that in this way there is no need for using a fluid inlet and outlet port to guide a sample or substance to a separated measurement region. The measurement region does not need to be enclosed by sensor walls. The number of mechanical sensor walls may be limited and optionally only at one side a mechanical sensor wall may be present. The miniaturization enables the device to be as compact that the natural flow of bodily fluids or the natural diffusion of substance, e.g. present in living creatures, e.g. in the human being, enable the possibility for sensing and for continuous monitoring the substance.

As indicated above, it is an advantage of embodiments of the present invention that sampling in a forced manner to a measurement region is not required. According to embodiments of the present invention, sampling may be obtained by natural flow or natural diffusion. In some embodiments, in order to prevent adhesion of particles, such as proteins, on the sensing surface and/or in order to prevent tissue growth onto the sensing surface, the sensing surface is protected. This can for example be done using a semi-permeable element, e.g. a membrane and/or layer, allowing the particles to be characterized to pass and blocking the particles that are not of interest. Some particular examples thereof will be illustrated below.

It is also an advantage of embodiments of the present invention that sensing is performed using optical characterization, therefore not requiring reagents. These advantages result in a reliable and long term usable sensor, without the need for significant interference of operators.

The sensor devices according to embodiments of the present invention can work in a free space mode, whereby radiation is directed into free space where the full radiation beam(s) has the chance of interacting with the particles to be detected. Alternatively, sensor devices according to embodiments of the present invention can work in an evanescent mode. Such a sensor advantageously may be waveguide based sensor. In one set of examples of evanescent spectrometers, the radiation, e.g. NIR light, travels e.g. through a waveguide, with a fraction of the optical mode located outside of this waveguide, this fraction being the evanescent part. This evanescent part can interact with the environment of the waveguide, just as in conventional free-space measurements. The optical spectra measured with an evanescent sensor contain the same or similar information about the medium as the spectra measured in free-space. The absorption spectrum of a fluid can thus be measured using a waveguide which is in contact with the fluid. In some examples, in order to increase the contact area, the waveguide may be spiral shaped, thus increasing the path length in the waveguide where the radiation is in contact with the sample. An advantage of embodiments being evanescent waveguides is that the power budget for an evanescent sensor can be better than for a free-space sensor, because coupling losses from the medium to the chip are avoided. Moreover, with an evanescent sensor the alignment and the implementation of e.g. a dual-beam spectrometer are easier. Evanescent sensors may, mutates mutandis, further comprise similar features and advantages as described for free-space sensors in embodiments of the present application.

The photonics integrated circuit according to embodiments of the present invention may comprise at least one multiplexer and/or one de-multiplexer. The multiplexer and/or demultiplexer may allow combining and/or splitting spectrally resolved radiation that will be processed, e.g. obtained from the spectrally processed radiation. It is an advantage of embodiments according to the present invention that by using a multiplexer and/or one demultiplexer, passage of the radiation through the substance to be sensed can be performed at a single position, resulting in accurate measurement and less noise, amongst others because of the fact that substantially the same substance can be sensed due to interaction of the radiation and the substance at one and the same physical position. In other words, a single optical path can be obtained for at least some of the spectrally resolved radiation that has been or will be processed prior to or after the interaction with the substance. In some embodiments, the sensor also may comprise a plurality of units, each having a multiplexer and/or demultiplexer for combining and/or splitting spectrally resolved information, so that optionally also different optical paths can be generated for different groups of spectrally processed radiation.

By way of illustration, embodiments of the present invention not being limited thereto, an example of a sensor device comprising standard and optional components according to embodiments of the present invention is shown in FIG. 1.

Figure 2A:
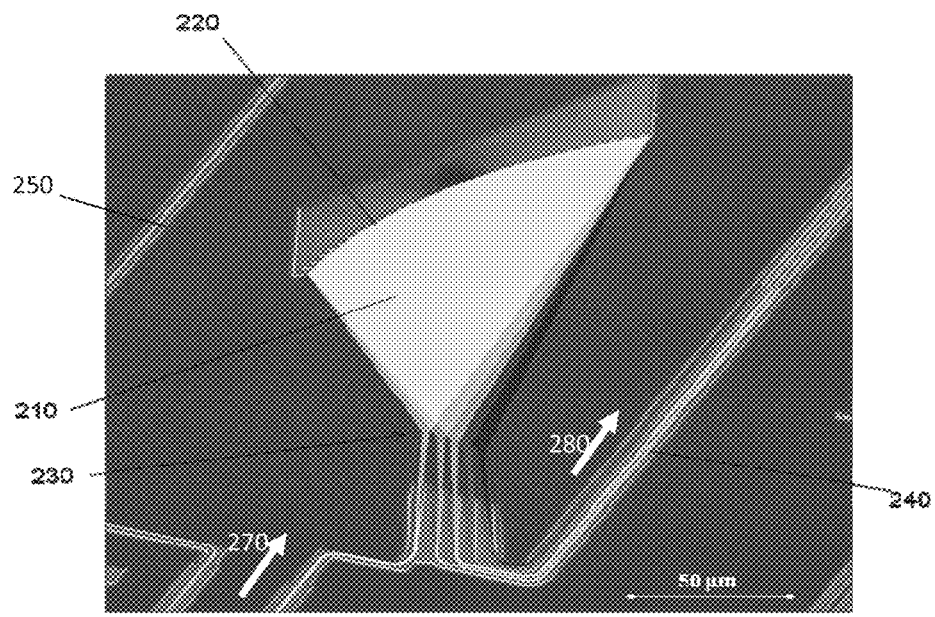
FIG. 2A illustrates a 1×4 demultiplexer based on a planar concave grating, as can be used in an embodiment according to the present invention.
Figure 2B:
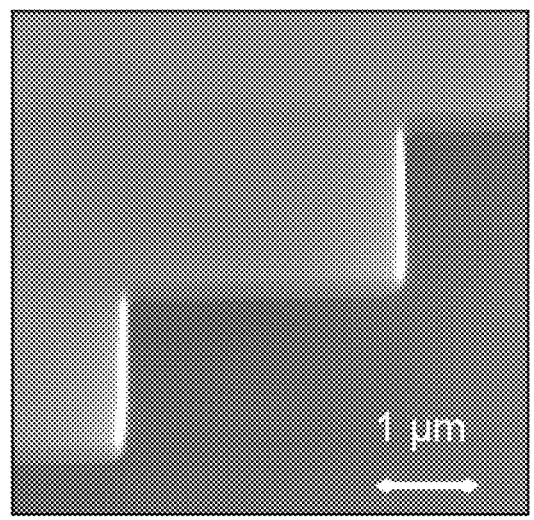
FIG. 2B illustrating an enlarged view of deeply etched teeth of an optical component as shown in FIG. 2A.
Figure 3:
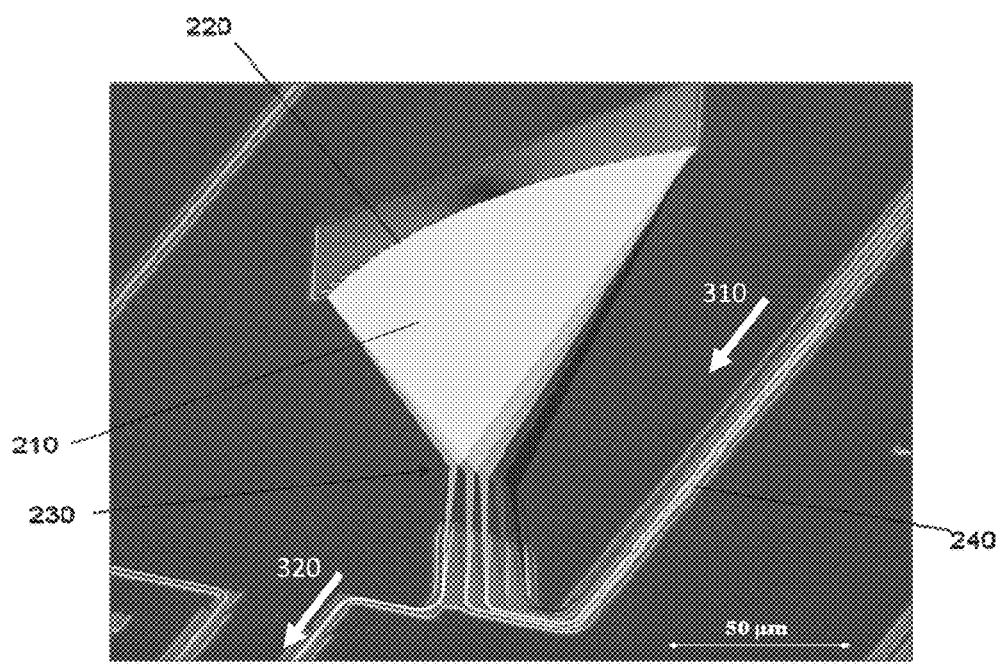
FIG. 3 illustrates a 1×4 multiplexer based on a planar concave grating, as can be used in an embodiment according to the present invention.

The sensor 100 according to embodiments of the present invention comprises a photonics integrated circuit, e.g. silicon photonics integrated circuit, based radiation processor 110. Such a photonics integrated circuit based radiation processor advantageously is adapted for processing radiation spectrally, prior to directing it to a sample, also referred to as pre-dispersive, and/or received after interaction with the sample, also referred to as post-dispersive, in such a manner that one or more corresponding detecting element(s) 120 is fed with appropriate signals. The photonics integrated circuit 110 and the detecting element 120 are described as separate components, but these may form one part. The photonics integrated circuit 110 therefore also may be part of the detecting element 120. The photonics integrated circuit 110 may comprise a plurality of integrated components, such as for example waveguides, multiplexers, demultiplexers, couplers, splitters, filters, tunable elements, laser sources, LEDs, etc. The photonics integrated circuit 110 is adapted for spectrally processing radiation, meaning that the photonics integrated circuit is adapted for processing the radiation in a wavelength dependent manner. In at least some embodiments of the present invention the photonics integrated circuit comprises optical components. The photonics integrated circuit 110 may for example act as a multiplexer or demultiplexer or part thereof, an interferometer or part thereof, an integrated active or passive optical cavity, an integrated optical active or passive resonator, an integrated optical coupler, a waveguide, a grating, or a combination thereof. The photonics integrated circuit may for example comprise a coupler for coupling in the radiation on the chip. One example of a coupler may be an on-chip diffraction grating. Such a diffraction grating may be optimized using optical design techniques. Examples of grating couplers that may be used are diffractive gratings with a 1 dimensional (1D) or 2 dimensional (2D) binary lattice structure. The couplers, e.g. gratings, capturing the radiation on the chip may be optimized for capturing the optimum amount of light, e.g. by increasing the coupler size and by matching the other coupler parameters thereto. Furthermore the coupler, e.g. grating may be adapted for splitting the spectrum into sub-ranges. An etched diffraction grating can be used that utilizes the coherence properties of light to spatially separate different wavelengths. The latter may be performed by using a coupler that comprises a number of individual sub-couplers each operating in a particular wavelength range being a sub-range of interest. Each coupler may be connected to its own radiation processor circuit. The circuit may be an interferometer, a tunable filter, an arrayed waveguide grating (AWG) or a planar concave grating (PCG) or a combination thereof. While the diffraction grating together with the circuit spatially separates the different wavelengths, photodetectors have to be integrated on the photonic chip to convert the optical signals into electrical signals. By way of illustration, a 1×4 de-multiplexer based on a planar concave grating is shown in FIG. 2A and a 1×4 multiplexer based on a planar concave grating is shown in FIG. 3. In the latter case, an integrated laser array might be coupled to the respective channels of the multiplexer. The de-multiplexer of FIG. 2A and multiplexer of FIG. 3 illustrate a structure with a reference photonic wire 250 wherein no dispersive processing occurs and a photonic wire 240, or photonic waveguide 240, respectively guiding radiation of different wavelengths away from or towards a spectrally processing radiation processor. In FIG. 2A, a set of 500 nm wide photonics wires is indicated for guiding radiation of different wavelengths away. The photonics integrated circuit of the de-multiplexer example is a structure having a dispersive concave grating, e.g. deeply etched teeth 220 also shown in enlarged view in FIG. 2B, for dispersively reflecting incident broadband radiation, a free propagation region 210 wherein the radiation can freely propagate and coupling structures 230, e.g. shallow-etch apertures, for coupling the dispersively reflected broadband radiation into the respective waveguides. The radiation processor in the multiplexer example is analogue due to reciprocity. In FIG. 2A arrow 270 gives the direction of the radiation coupling in the radiation processor and arrow 280 indicates the direction of the radiation being coupled out of the radiation processor. In FIG. 3 arrow 310 gives the direction of the radiation coupling in the photonics integrated circuit and arrow 320 indicates the direction of the radiation being coupled out of the photonics integrated circuit.

Figure 4:
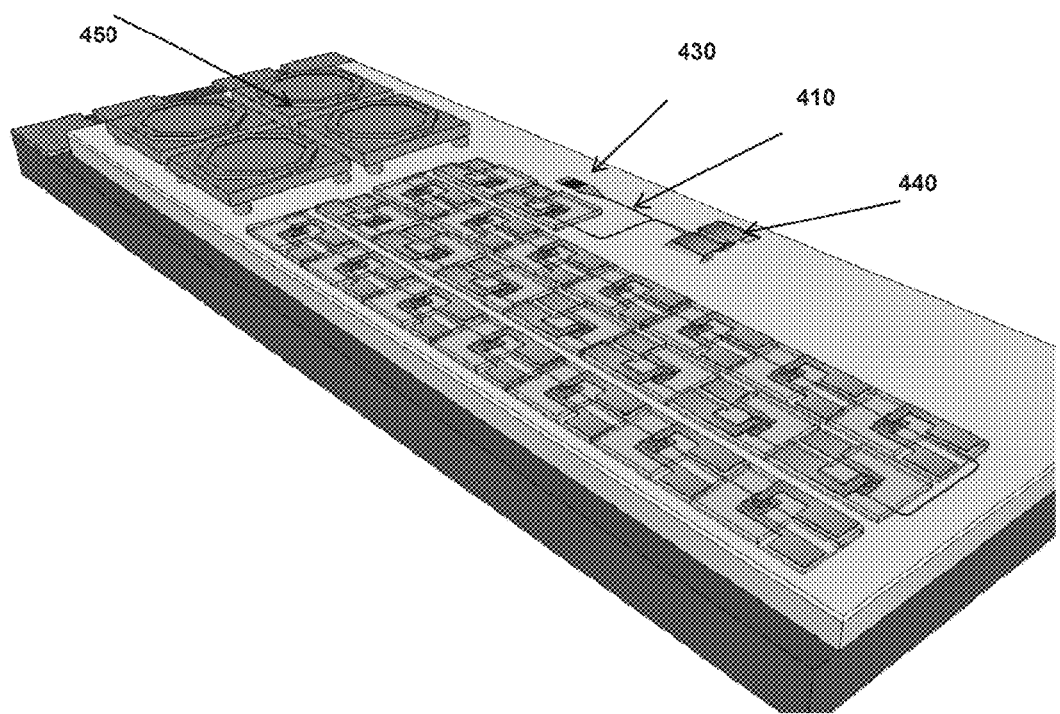
FIG. 4 illustrates a 1×23 multiplexer based on a laser array coupling to a waveguide, as can be used in an embodiment according to the present invention.
Figure 5:
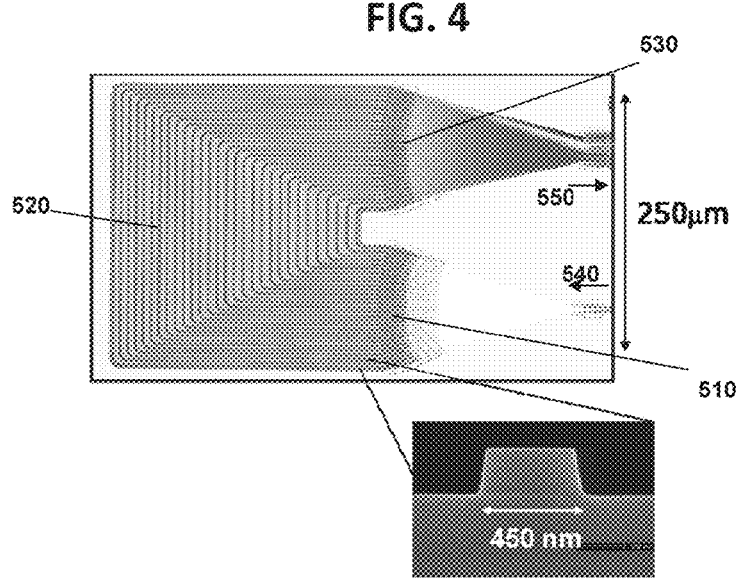
FIG. 5 illustrates a 1×32 demultiplexer based on an arrayed waveguide grating, as can be used in an embodiment according to the present invention.

FIG. 4 and FIG. 5 illustrate a 1×23 multiplexer and a 1×32 de-multiplexer respectively de-multiplexer. The multiplexer 400 in FIG. 4 is based on integrated lasers 410, e.g. silicon photonics integrated lasers, e.g. ring lasers or micro disk lasers or DFB lasers or DBR lasers, and light is directly coupled in a single silicon waveguide 420, such that serial multiplexing is intrinsic when using a PIC technology approach. Alternatively, also coupling of radiation from some or all of the integrated radiation sources to different waveguides may be used. A laser array of 23 lasers is shown as example in FIG. 4. The lasers may be tunable lasers, in the present example each covering about 2 to 4 nm wavelength range. The light of the respective lasers are serially multiplexed on a single waveguide and coupled out of the circuit by a coupling element e.g. grating coupler 430. A monitoring diode might be integrated, i.e. the integrated power monitor 440, to monitor the circuit. Furthermore, sensitive photodetectors 450 for detecting the radiation after interaction with the object under study is also shown.

The 1×32 de-multiplexer shown in FIG. 5 is based on an arrayed waveguide grating. An input coupler, such as for example an input star coupler 510, and an output coupler 530, such as for example an output star coupler, are used for guiding the radiation to the photonics integrated circuit, whereby the photonics integrated circuit in this configuration comprises an arrayed waveguide grating (AWG), which introduces a wavelength dependent phase delay. A set of dispersive delay lines 520 is shown. Depending on the number of channels and the width of the wavelength channels, either an AWG or a PCG is preferable in terms of performance or size. Arrow 540 indicates the in coupling direction for the radiation, while arrow 550 indicates the out coupling direction for the radiation. By way of illustration a possible size of a delay line is indicated using a picture, embodiments of the invention not being limited thereby.

Alternatively to a PCG or AWG based multiplexer, grating couplers to spatially multiplex the light of an integrated laser array might be used, or multiplexing by serially coupling the lasers to a single waveguide might be used. This approach is enabled by the fact that a photonic integrated circuit technology is used. Waveguides and gratings can be used to guide the light and couple the light out/in wherever necessary.

According to other embodiments of the present invention, the photonics integrated circuit may comprise optical components that merge or split different spectral radiation components of the radiation beam. The sensor 100 furthermore may comprise one or more detecting elements 120 for detecting the processed radiation. Such one or more detecting elements 120 are photonics integrated circuit compatible detecting elements. The detecting elements 120 may for example be III-V material based detecting elements that can be integrated in the photonic integrated circuit platform. Integration of the detecting element may be performed in a number of ways: the detecting elements 120 may be monolithically, heterogeneously or hybridly integrated with photonics integrated circuit 110 or coupled through optical fibre to the photonics integrated circuit 110. In one example, one or more detecting elements 120 may be based on epitaxial grown layers or wafers, although the invention is not limited thereto. Conventional or designed bonding processes may be used for integrating the detecting elements. In case of a glucose sensor, the detecting element 120 may for example be an InGaAs epilayer detector, which is especially suitable in the overtone band, or an InGaAsSb epilayer detector which may be especially suitable for the combination band. Other detecting elements also could be used, as long as these can be integrated within the photonics integrated circuit platform in a suitable manner and as long as their detection characteristics are suitable for the sensing requirements set.

The sensor 100 also may comprise at least one radiation source 130 for generating a radiation beam for irradiating a sample. The radiation source may be integrated in the photonics device. The radiation source may be a single radiation source or may be an array of sources, such as for example an array of lasers or a laser array. The at least one radiation source 130 advantageously is a photonics integrated circuit compatible radiation source integrated in the sensor, although integration of the source on the photonics integrated circuit is not essential. In one embodiment, the at least one radiation source 130 may be homogeneously integrated with the sensor, for example with the photonics integrated circuit 110 as shown in FIG. 4 or heterogeneously integrated with the sensor 100, for example with the photonics integrated circuit 110, although the invention is not limited thereto. The radiation source may be adapted for irradiating the sample in a wavelength range that is suitable for sensing the substance under study, e.g. in the overtone or combination band. In one embodiment, the radiation source may be a light emitting device (LED) integrated in a photonics integrated circuit platform used in the sensor 100. The radiation source 130 also may be any other suitable radiation source, such as for example a VCSEL, a solid state tunable laser, etc. Due to the small emission wavelength range wherein most tunable radiation sources can be tuned, the radiation source preferably is a wide wavelength range emitting radiation source or a laser array, covering a suitable range for characterizing substances.

The measurement configuration and principle of the sensor 100 typically may be defined by the detecting element, the photonics integrated circuit or part thereof and optionally also the radiation source. The sensor configuration may be adapted to accommodate for example spectral absorption measurements, spectral reflection measurements, spectral transmission measurements, spectral transflective measurements, spectral scattering measurements, Raman spectroscopy measurements, optical coherence tomography, spectrally resolved optical coherence tomography, spatially resolved diffuse reflectance spectroscopy measurements, spatially resolved measurements or a combination thereof. Advantageously, embodiments of the present invention include a sensor configuration wherein the detected results are spectrally resolved, comprise depth-related information or preferably a combination thereof. It is an advantage of some embodiments according to the present invention that advanced photonics integrated circuits can be provided allowing both spectral and spatial in-depth analysis and resulting in good sensors. Such advanced photonics integrated circuits allow for compact sensors with high accuracy.

Obtaining depth-related information is especially suitable e.g. in case the response comes from a diffusely scattering medium. The latter may be especially suitable for sensing of media of interest separated from the sensor by tissue, such as for example collagen deposits. By way of illustration, a number of sensor configurations allowing particular measurement techniques will be described further in the description.

The sensor 100 may have a measurement chamber or measurement region 140 or may be adapted for measuring in an external measurement region 140. The position of the measurement region 140 typically may be determined by the sensor configuration. In case the sensor configuration allows measurement in transmissive or transflective measurement, the measurement region typically may be surrounded by components of the sensor. Typically in such measurements, the at least one radiation source 130 is substantially diametrically opposed to the detecting element 120. Or in a pre-dispersive approach, the at least one radiation source is substantially diametrically opposed to the detecting element. Alternatively, the radiation source may be integrated in the photonics integrated circuit platform and an additional mirror opposed substantially diametrically to the radiation source with respect to the measurement region 140 directs radiation that has passed the sample towards the photonics integrated circuit. In such a setup, the measurement system detects both the diffuse reflectance and the transmittance signal, which may be especially suitable in case dense biological suspensions are to be measured. In case a sensor with a measurement region surrounded by components is selected, the size of the measurement region, which typically may correspond with the internal diameter of the sensor through which the sample may pass, must be determined as function of the absorption coefficient of the sample or tissue relative to the absorption coefficient of glucose and the available power budget. By way of example for the combination band, an optical path length may be preferred between 1 mm and 2 mm, implying an inner diameter between 0.5 mm and 2 mm. One possible shape is a ring shape or doughnut shape, although the invention is not limited thereto. By implementing the sensor as a photonic integrated circuit based sensor a miniaturized sensor can be obtained having a small foot print in the order of square mm. The overall average diameter of the sensor may for example be in the range 4 mm to 50 mm. In case the sensor configuration is adapted for measuring in reflection, the measurement region 140 typically lies outside the solid portion of the sensor, i.e. on one and the same side of the sensor components. Diffuse scattered light then can be detected. The actual preferred sensor shape may be defined by a number of factors, e.g. the chosen configuration such as measurement in reflection or in transmission, the body reaction—which shape causes the least tissue reaction—, etc. and can be chosen as function of the weight of these factors, e.g. a cylinder with height 0.5-30 mm and diameter order 2-50 mm.

It is an advantage of embodiments according to the present invention that measurement regions without inlet and outlet, e.g. measurement regions being not substantially limited by walls of the sensor, can be used. The latter allows quick measurement of the substance, optionally reducing the instrumental delay time between actual concentration of the target analyte in the sample and the measured concentration of target analyte in the sample.

The required signal-to-noise ratio, the number of spectral measurements, the necessary resolution may depend on the sample, e.g. tissue that is measured and may for example be determined based on trial and error, a complex tissue model, by experimental test measurements, etc. The obtained signal to noise ratio SNR depend on the magnitude of the radiant power reaching the detector. As the thickness increases, the radiant power at the detector decreases because of scattering and absorption processes. The concentration sensitivity for the detection typically increases linearly with tissue thickness while the signal to noise ratio decreases exponentially. The sensor may be designed such that the spectrometric performance and power budget may be optimized, taking into account parameters such as the bandwidth, the resolution and sensitivity, etc.

The sensor 100 furthermore may comprise an electronic unit 150 for controlling and driving the radiation source 130 and/or the sensing elements 120. The electronic unit may be implemented in CMOS technology. Furthermore if tunable components are present in the photonics integrated circuit 110, these also may be driven by an electronic unit 150. The electronic unit may combine a plurality of control or drive functions or separate electronic units may be provided for each component to be driven. It is an advantage of embodiments according to the present invention that the electronic unit 150 optionally may be integrated in the same photonic integrated circuit chip as used for the radiation source 130 and the sensing elements 120. Thus, although the invention is not limited thereto, the electronic unit may be integrated with the photonic integrated circuit. Such integration may be monolithically, i.e. electronics and photonics can be defined in the same process flow whereby either the photonics components or the electronics components can be performed in front-end processing. Alternatively, heterogeneous integration may be performed whereby the photonics wafer and the electronics wafer are processed in separate process flows and are then integrated. The electronic unit may be connected with the components to be controlled through interconnections, e.g. vias. In an advantageous embodiment, the electronic unit and the components may be stacked and connection may be performed by throughput vias e.g. cupper nails. Other ways of integration may include bonding techniques such as for example BCB or wafer bonding, whereby both die to wafer or wafer to wafer bonding may be performed. Alternatively, the photonic integrated chip and the electronic chip can be positioned close to each other on a printed circuit board, e.g. a thin flexible printed circuit board. The latter may be done prior or after packaging. The electronic unit may control components according to a predetermined algorithm, a programmable algorithm, preferably programmable from a distance, etc. The electronic unit may comprise a power source, e.g. battery, e.g. inductively powered, so that powering of the system can be performed from a distance.

The sensor 100 furthermore may comprise a data transmitter 160, for transmitting data from the sensing element(s) 120 to a read-out component outside the body. The data transmitter may comprise a memory for temporary storing the data before sending. The data transmitter 160 thus typically is linked through the sensing element(s) 120 for capturing data from the sensing elements. Nevertheless, other components, such as for example the electronic circuit or additional sensing elements present in the sensor, e.g. T-sensor, humidity sensor (e.g. detecting leakage), etc. also may be connected to the data transmitter for passing information to an external read-out component. Data to be transmitted may for example involve absorption, reflection, transmission or scattering data obtained with the sensor, timing data, data for reporting functionality of the sensor, etc. The data transmitter 160 also typically may comprise an antenna for transmitting the data.

The sensor may be packaged in a biocompatible packaging 170 such that good implantation properties are obtained. The latter may be a biocompatible packaging as known from prior art or a more dedicated biocompatible packaging, specifically designed for the sensor. The sensor may be packaged such that it is transparent for incident radiation. The packaging may also enable a bio-mimic interface with its environment. The packaging may for example comprise one or more layers being an impermeable cover. Such a cover may e.g. be present at only that part of the chip where no interaction with the sample is required.

Whereas according to some embodiments of the present invention the sensor may be adapted such that it can operate in a pump-free manner, the system may be adapted such that it nevertheless can be used with an extraction system for extracting bodily fluid using e.g. current or micro-cannula, with a micro dialysis probe, with an ultra-filtration probe, etc. The sensor could e.g. then be used to perform measurements on small amounts of bodily fluid, e.g. interstitial fluid extracted to a measurement chamber. Nevertheless, such embodiments may suffer from being less reliable with respect to long-term use.

Figure 6:
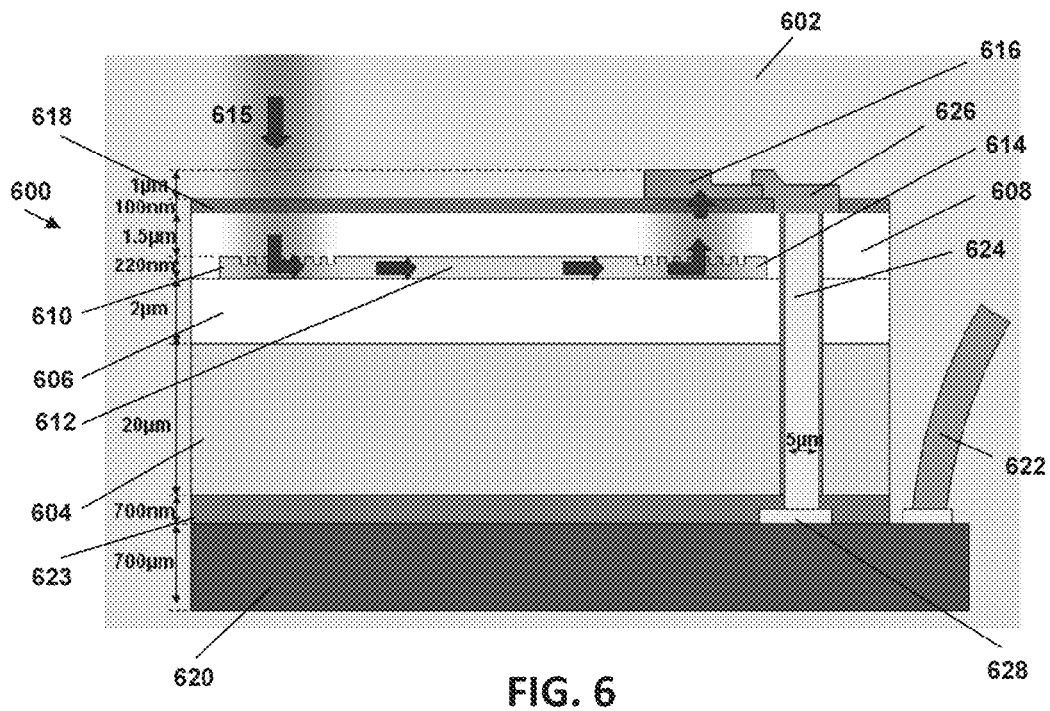
FIG. 6 is a schematic cross-section of an exemplary post-dispersive sensor according to one embodiment of the present invention.
Figure 7:
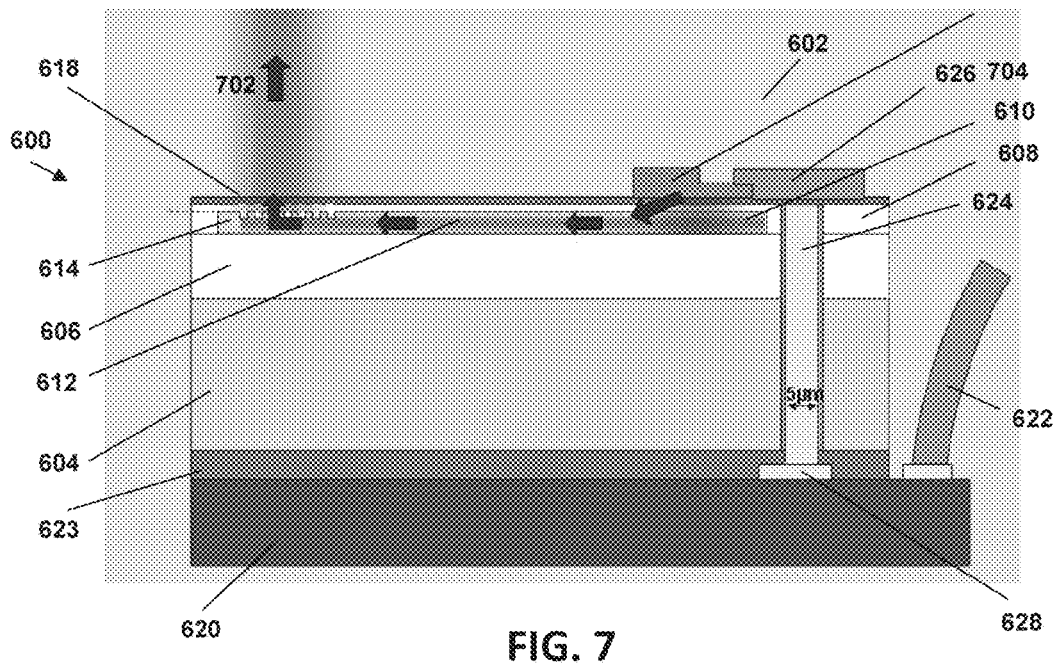
FIG. 7 is a schematic cross-section of an exemplary pre-dispersive sensor according to one embodiment of the present invention.

By way of illustration, a schematic cross-section of a sensor comprising a silicon photonics integrated circuit and detecting element resulting in an integrated spectrometer is described with reference to FIGS. 6 and 7 for a post-dispersive respectively pre-dispersive sensor, the present invention not being limited thereto. The illustrated sensor 600 shows a device packaged in a biocompatible packaging material 602. The photonics integrated circuit based sensor 600 comprises a silicon substrate 604, whereon an oxide layer 606, whereon a silicon layer and an oxide top cladding layer 608 is provided. In these materials an input grating 610, a waveguide 612 and an output grating 614 are provided being part of an optical processor and allowing incoupling of incident radiation 615 and direction of the radiation towards a detecting element 616, in the present example being a III-V detector, e.g. InGaAsSb. In the present example, the detecting element 616 is provided on the oxide layer 606 using a BCB bonding layer 618. Furthermore, at a backside of the silicon substrate CMOS electronics 620 are provided comprising drivers for driving the detecting element, the radiation source, the tunable components, the data conversion means and transmission means for transmitting the data. The latter also is provided via a BCB bonding layer 623. Powering of the detecting element may be performed through a Cu nail through via 624 connected with the CMOS electronics which may be powered through a connection wire 622, or more preferably wireless. The through via may comprise a Au metallization 626 for actually connecting the through via with the detecting element, and at the other side may be connected with the CMOS electronics driver component via a Cu landing pad 628. Similar components can be seen in FIG. 7, but the component shown is a component for irradiating tissue whereby radiation is coupled out 702 and therefore a radiation source 704, in the present example being a laser, is provided coupling light into a waveguide and coupling out the radiation to tissue.

In order to further illustrate the principles and features of different embodiments of the present invention, a number of particular embodiments will be discussed in detail below.

In one particular embodiment, the sensor is adapted for spectral absorption, reflection or transmission measurements or for use with spectrally resolved scattering measurements. The sensor according to the particular embodiment therefore may comprise an integrated spectrometer that can measure the intensity of radiation in small wavelength intervals. The integrated spectrometer is then formed by the photonics integrated circuit 110 and the detecting element 120. In order to obtain the integrated spectrometer, the photonics integrated circuit 110 may comprise an on-chip wavelength demultiplexer which separates incoming radiation, after it has interacted with the sample, into its constituent wavelengths. The multiplexer and demultiplexer may be based on several techniques, such as for example resonators, diffraction gratings, dispersive delay lines, etc.

Figure 8:
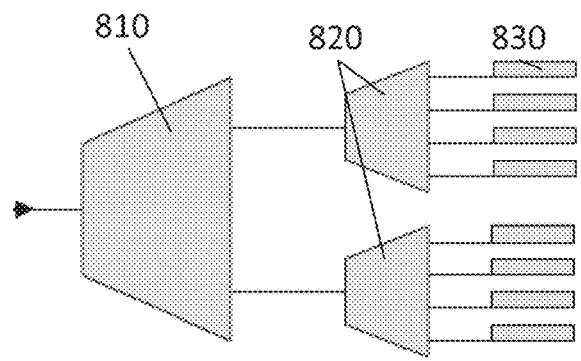
FIG. 8 to FIG. 11 illustrate different examples of radiation processors, as can be used in embodiments of the present invention.
Figure 9:
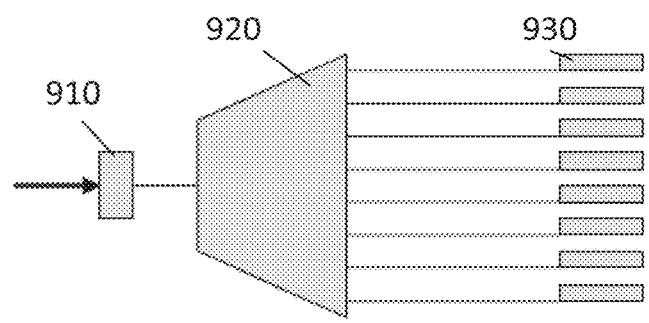
Figure 10:
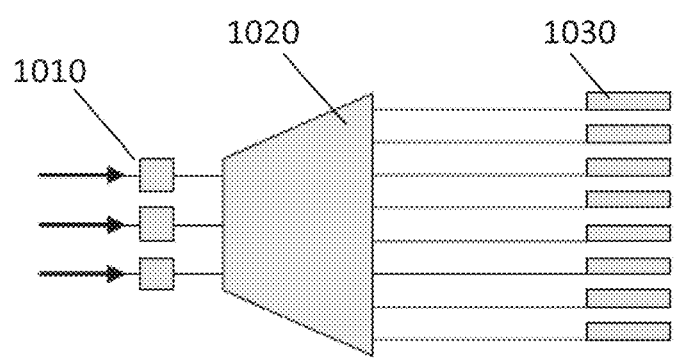
Figure 11:
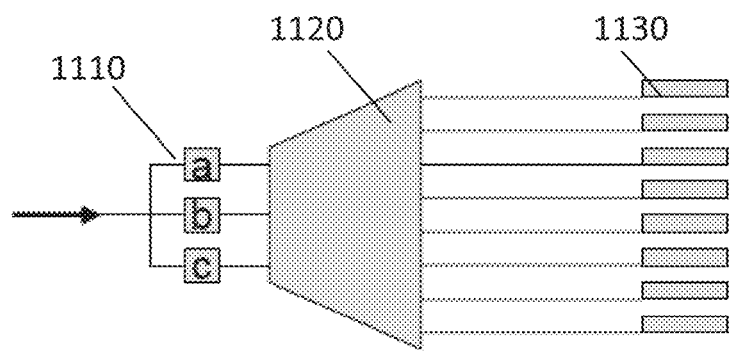
Figure 12:
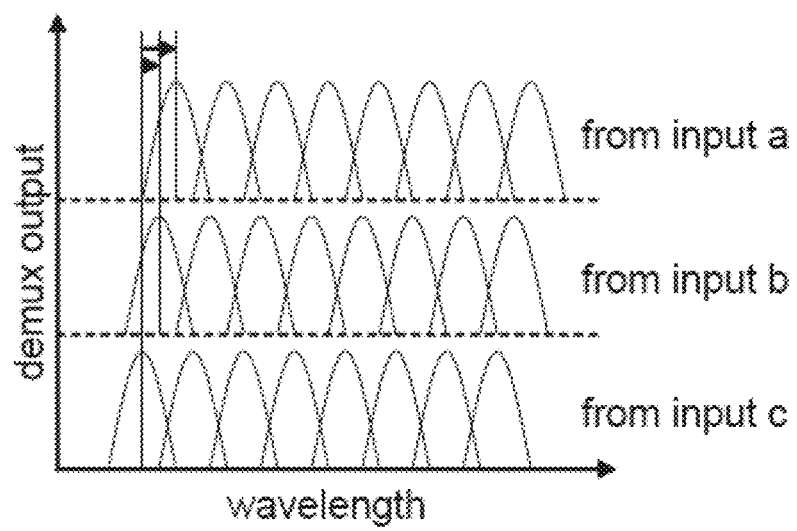
FIG. 12 illustrates the Vernier shift obtained in spectra when using a Vernier demultiplexer according to one embodiment of the present invention.

In further particular embodiments, the sensor is adapted for spectral measurements using an integrated spectrometer, whereby an increased number of channels compared to conventional spectrometers is obtained using one or more of the following techniques. A large number of wavelength channels in the spectrometer increases the resolution obtained. A number of techniques may advantageously be used to enlarge the resolution, further allowing to limit or prevent the increase of crosstalk levels. These techniques also may be combined with each other. The photonics integrated circuit may comprise cascading wavelength demultiplexers. Instead of splitting the spectrum in one operation, first a coarse splitting may be done, followed by a set of finer splitting with narrower wavelengths. In one example, the coarse splitting can be performed by grating couplers, i.e. by a first demultiplexer 810, while the narrower channel splitting can be done using an arrayed waveguide grating (AWG) or a planar concave grating (PCG), i.e. by second demultiplexers 820. The split radiation is guided to a plurality of detector elements 830. The latter is shown in FIG. 8. The photonics integrated circuit also may comprise cascading using swept tunable filters 910 and a demultiplexer 920: for finer resolution, the input or output of the spectrometer could be connected to a sharp wavelength filter, which is tunable. By rapidly sweeping the filter and measuring the response a higher-resolution spectrum can be obtained which can be detected by detectors 930. The latter is shown schematically in FIG. 9. A third technique that may be used for having a large number of channels is frequency or time-domain multiplexing the use of the spectrometer. Several types of spectrometers (especially the arrayed waveguide grating based spectrometers) can have multiple inputs, in fact about the same number as there are outputs. Using all inputs at the same time will blend together the spectra of all the inputs. This can be remedied by using fast switching at the inputs, so all inputs can be processed using the same spectrometer one at a time. Similarly, the signals at all the inputs could be modulated using a different RF frequency, which can then be split again by the electronics at the detector side. In this way more channels can be generated. The principle is illustrated in FIG. 10, illustrating a set of switches/modulators 1010 at the receiving side, followed by a demultiplexer 1020 and a set of detectors and demodulators 1030. A fourth exemplary method for increasing the number of channels may be by exploiting the Vernier-shifted spectral response, as illustrated in FIGS. 11 and 12. In FIG. 11 a set of switches/modulators 1110 is shown directing radiation to a vernier demultiplexer 1120 and guiding radiation to a set of detectors 1130. FIG. 12 illustrates the demultiplexer output as function of wavelength for the different switches/modulators a, b and c shown in FIG. 11. Based on the previous technique, the same input could be analysed in more detail by inducing a Vernier-shifted spectral response. By carefully designing the spacing of the inputs and outputs, the spectral position of the output wavelength channels can be shifted for the different outputs. By combining the data from the different inputs, a much more detailed spectrum can be obtained. Or, in reverse, the channel count of the spectrometer could be reduced and still yield the same information. Advantageously, a sensor according to the present embodiment is equipped with a spectrometer that can handle up to 40-60 wavelength channels with 2-3 nm resolution. In one example, a spectrometer platform, potentially low-cost, which can handle several tens of wavelength channels and >0.5 nm channel spacing is obtained.

Figure 13:
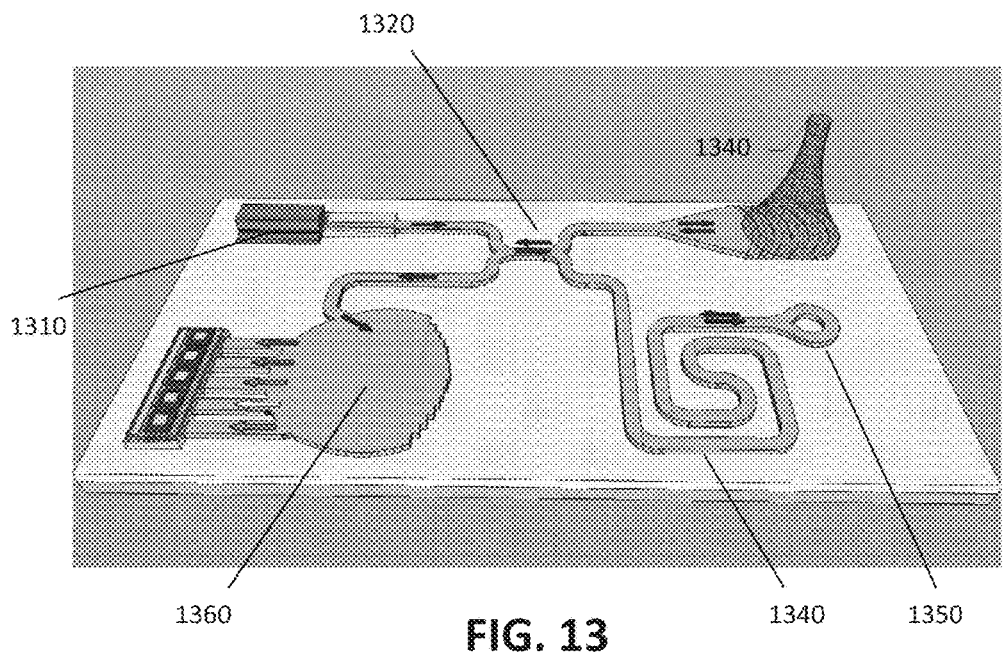
FIG. 13 illustrates a basic setup for an optical tomography system as can be used in embodiments according to the present invention.

In one particular embodiment, a sensor using optical coherence tomography is envisaged. In one example, an optical coherence tomography (OCT) based sensor comprises a simple Michelson interferometer with a low temporal coherence source in one arm, a second reference arm, an object under study in the third arm and a registering element or spectrometer in the fourth arm. The source radiation is divided into the two arms and the backscattered light is interfered with the reference arm. A schematic drawing is shown in FIG. 13, indicating a radiation source 1310 in the present example being a superluminescent diode, a splitter 1320 splitting the radiation in one part directed to the sample through a focus point 1330 and a second part provided in a delay line 1340 in the present example being based on a loop mirror 1350. A combiner 1320 also typically is present (this may be the splitter) for combining the two parts of the radiation beam again whereby the radiation then is directed to a spectrometer 1360. Appropriate interferometric signals in an OCT system can be formed when the optical path length in the sample arm matches that in the reference arm within the coherence length of the source. The interference in OCT amplifies the backscattered signal and increases the sensitivity limit of the detection. In order to achieve a high resolution and depth range, a broadband radiation source, for example with a 100 nm bandwidth, may be used in combination with a high resolution spectrometer with a detector array of e.g. 1024 pixels. The bandwidth determines the axial resolution, and the imaging depth is either limited by attenuation of the medium or spectrometer resolution of the system.

The sensor may consist of a group of sensors as described above. Alternatively or in addition thereto a sensor may comprise a plurality of detecting devices, e.g. a 1D or 2D array of detecting devices.

In a further particular embodiment, a sensor is adapted for performing spectrally resolved optical coherence tomography. The latter allows analyzing spectra of backscattered light a depth-resolved manner. SOCT is an extension of OCT imaging, analyzes not only the intensities, but also the spectra of backscattered light in a depth-resolved manner. This technique is capable of both qualitative contrast enhancement and quantitative concentration measurement. The system is based on a system as described above, whereby the interference spectrum is not fully combined in the processing, but whereby the interference spectrum is divided, prior to Fourier transforming the spectrum, into several windows, each window being used to estimate the depth profile. The method implies a trade of between the axial resolution and obtaining wavelength dependent, depth resolved measurements. For some applications, depending on the volume distribution of the analyte, it may not be necessary to achieve very high spatial resolution, and few hundred microns axial resolution would be sufficient. Thus, sources with much smaller bandwidths can be used, or the spectrum can be analyzed by dividing it into smaller spectral windows. Windowing of the interference spectrum may be done using multiple demultiplexers, tunable filters, high resolution spectrometers, etc, some of these methods being discussed above.

Whereas embodiments are described for detecting substrate in a sample, a sensor for imaging a substrate, e.g. tissue, using optical coherence tomography in in-vivo is also envisaged by embodiments of the present invention. The latter may for example be used for imaging tissue using the scattering occurring when irradiating tissue. It therefore may provide a physionomical imaging of the tissue.

In another particular embodiment, a sensor is described for absorption, scattering, reflection of transmission measurements, whereby a coupler in the optical processor may be used for extracting spatial information. The coupler may for example be a grating coupler. As the wavelength range coupled in is dependent on the angle of incidence of the radiation, from the detected spectrum an estimate of the incident angle of the radiation can be made, whereby the latter can be coupled to the origin or the optical path length that has been travelled in the tissue. Optimisation of the coupler, e.g. grating coupler may be performed using numerical simulation.

In still another embodiment, a sensor is provided with a spatially resolved spectroscopic setup. The object is illuminated at one position and the reflectance and/or backscattering is measured at different distances from the source. The signals captured and representative for different depths of the sample are detected by different detecting elements, resulting in a spatially resolved image.

The sensor may be powered in any suitable way, such as for example via a battery which could for example be powered inductively. Energy and power provision, control and use may be based on energy harvesting, e.g. energy scavenging. Furthermore data transmission from and to but also within the sensor may be performed in a wired or more preferably a wireless manner.

Figure 16:
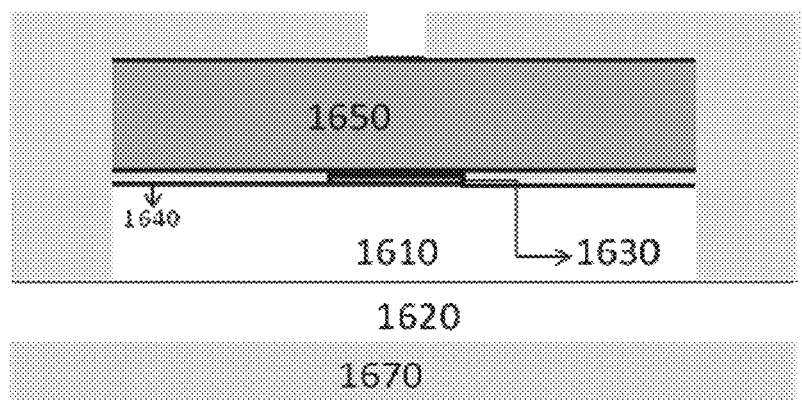
FIG. 16 to FIG. 18 illustrate examples of sensors wherein an evanescent spectrometry setup is used, according to embodiments of the present invention.
Figure 17:
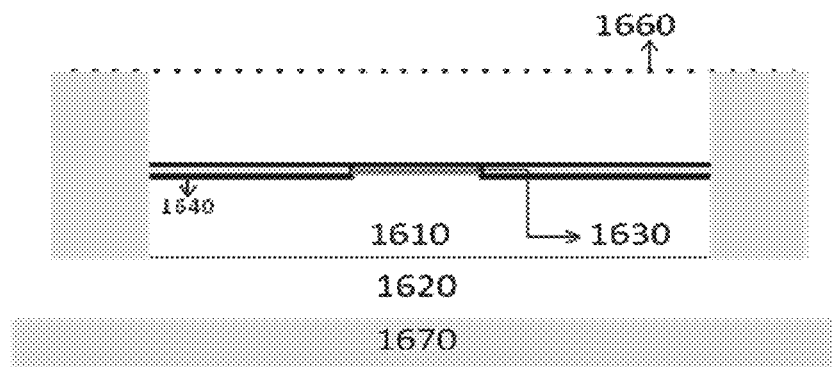
Figure 18:
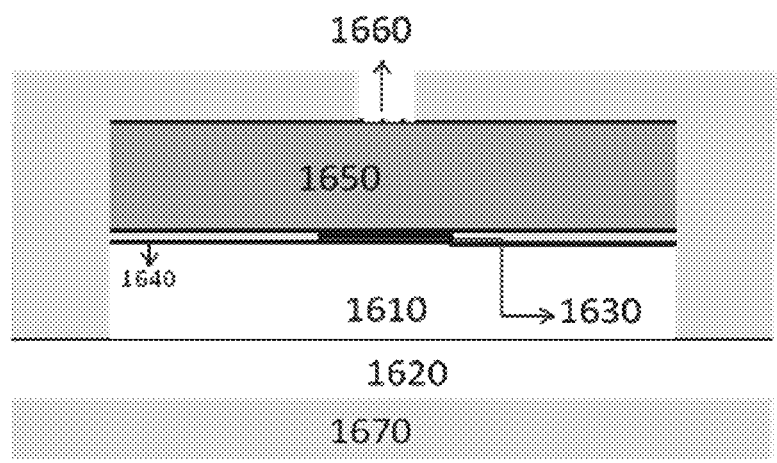

By way of illustration, further sensors according to some embodiments of the present invention are now discussed with reference to FIG. 16 to FIG. 18, the sensors being evanescent sensing spectrometers. The sensors 1600, 1700, 1800 shown are waveguide based. In the particular examples shown, a silicon on insulator photonics integrated circuit 1610 for spectrally processing radiation interacting with the substance is introduced on a carrier or an electronic platform 1620. The waveguide 1630 in the current examples has a spiral shape, although embodiments of the present invention are not limited thereto. The other parts of the photonics integrated circuit 1610 may be covered with an impermeable cover 1640. In the examples shown, in order to prevent adhesion of particles and tissue growth, a semi-permeable element is used to protect the sensor. In FIG. 16, the semi-permeable element is a layer 1650, in the present example be a hydrogel, covering the photonics integrated circuit 1610. In the present example, the layer is directly on top of the sensor surface. In another example, as shown in FIG. 17, the semi-permeable element is a membrane 1660, at a small distance separated from the sensor surface. In the example shown in FIG. 18, both a layer 1650 and a membrane 1660 are present. The carrier or electronic platform 1620 also may be covered with a biocompatible coating 1670. It is an advantage of embodiments according to the present invention that by using evanescent sensing a sensor with a good power budget is obtained. The latter is especially advantageous in implantable sensors where powering is an important issue.

Another example, similar to the evanescent sensing spectrometers discussed above, is an evanescent sensing dual-beam spectrometer. Such a waveguide-based spectrometer can be implemented by making two, e.g. spiral-shaped, waveguides on the same photonics integrated circuit. In one example, the reference spiral can be covered with a medium whose optical properties are similar to that in the signal arm, e.g. water or hydrogel, and shielded from the glucose-containing fluid to provide a stable reference measurement.

Figure 14:
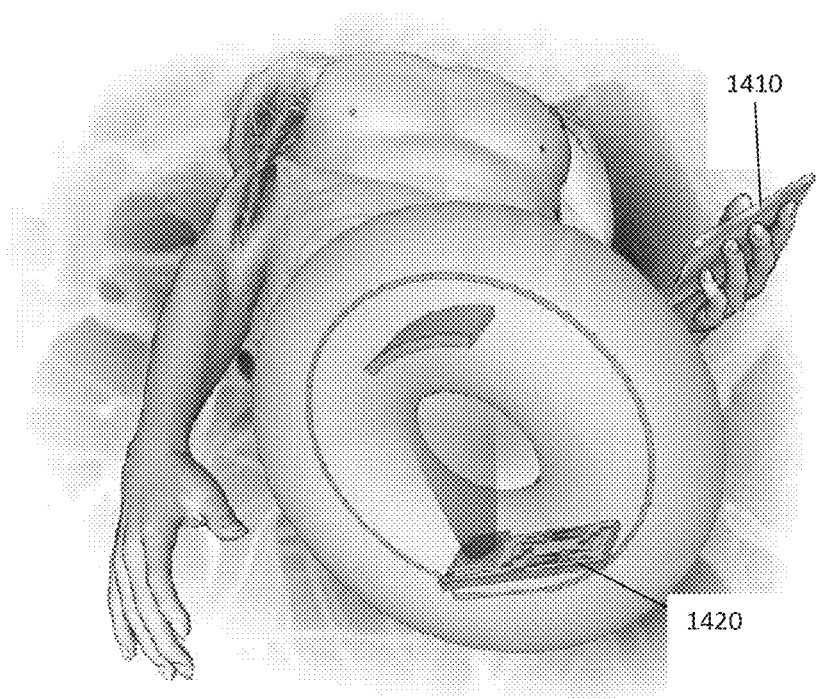
FIG. 14 and FIG. 15 illustrates an example of a continuous monitoring system according to an embodiment of the present invention.
Figure 15:
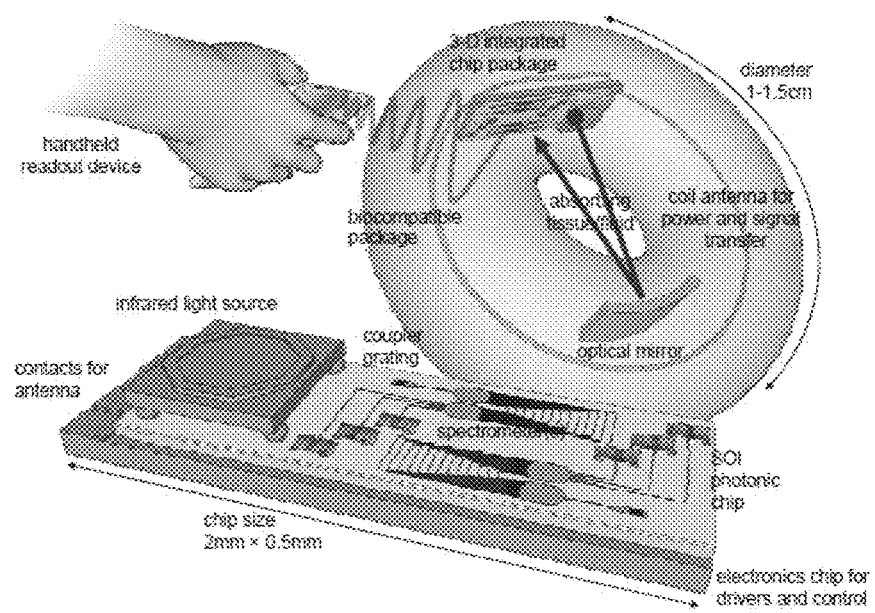

In one aspect of the present invention, a continuous monitor—also referred to as continuous monitoring system—is described. Such a continuous monitor comprises a sensor as described in the first aspect. The continuous monitoring system may be a continuous glucose monitoring system. The sensor may comprise the same features and advantages as set out in the first aspect. The continuous glucose monitor may also include power electronics and data-transmission electronics for powering the device and for outputting data. These components may preferably be incorporated in the sensor, although the invention is not limited thereto. The power electronics may be inductive power electronics such that the sensor can be easily powered, without the need for surgical intervention or electrical contacts in mechanical contact with the sensor and present on the body. The data transmission electronics may be adapted for corresponding in a wireless manner with an external device. Such data may for example involve absorption or scattering data obtained with the sensor, timing data, data for reporting functionality of the sensor, etc. An example of a continuous glucose monitoring system is shown in FIGS. 14 and 15. The present invention not being limited thereto. FIG. 14 illustrates a biocompatible packaged single-chip optical spectrometric sensor 1420, together with inductive power and wireless data-transmission electronics being implanted, e.g. subcutaneously in the upper arm. The sensor according to the present example is fed by and communicated with an external, wearable or portable read-out device 1410. In one example, the sensor may be coupled with an automatic insulin infusion system to enable a "closed loop" control, i.e. using an artificial pancreas system. The sensor may detect absorption or scattering in a measurement region close to the sensor, whereby no particular inlet or outlet is required. The latter may be advantageous, as the absence of inlet and outlet ports may result in better passage and reduced obstruction of the flow of the sample. FIG. 15 illustrate an overview for an implanted biosensor, indicating a handheld readout device wirelessly connected to 3D integrated chip package, enclosed in a biocompatible package, the package also comprising the coil antenna for power and signal transfer, an optical mirror for reflecting the optical signal in the current exemplary measurement setup and a measurement region comprising absorbing tissue or fluid. The diameter of the package typically may be in the range of 1 to 1.5 cm, although embodiments of the present invention are not limited thereto. A more detailed picture of the 3-D integrated chip package also is shown, indicating an infrared light source, a coupler grating, a spectrometer portion, a SOI photonic chip and an electronics chip for driving and controlling. An example of a chip size may be in the range 2 mm×0.5 mm, although embodiments of the present invention are not limited thereto.

In one aspect, the present invention also relates to the use of a sensor as described above or a continuous monitoring system as described above for sensing a substance, e.g. glucose in the body of a living creature. It is an advantage of such use that results can be obtained in a rapid and accurate manner, and in an automated and/or automatic way such that monitoring of the substance level can be done more appropriately.

Fabrication of the spectrometric sensor by e-beam or a photolithographic process, using CMOS technology, using silicon technology, and semiconductor etching steps and back-end process steps like flip-chipping, bonding, metallisation are well described in literature and state-of-the-art technology. Processing of the dispersive sensor components, such as for example of the photonics integrated circuit, the detecting element, gratings, waveguides, the at least one radiation source, and/or the memory may thus be based on conventionally known techniques, although also more complex processing techniques described in literature may be applied.

Also the wireless unit is based on state-of-the-art technology. There are a lot of wireless communication standards like Zigbee, Bluetooth, Wibree, UWB etc. available on the market. Most of them are low power solutions and available in a small form factor. Depending on the application, e.g. read-out scanning rate, a power range and databit range, a communication protocol can be selected. A driver chip implementing the communication protocol will be connected to the spectroscopic chip or integrated to a single chip, e.g. via 3D packaging or the communication electronics might be homogeneously integrated with the photonics on a single chip e.g. in case of silicon photonics. Fabrication of electronic chips is well known to the skilled person.

Wireless power transmission based on inductive coupled coils might power the system. Wireless power transmission in the lower frequency band is well known with RFID applications. Depending on the application and related read-out scan rate, the power needed for the photonic sensor system might be much more than current RFID Transponder require, e.g. a power of 300 mW-3 W. Custom developed inductively coupled coils might be integrated, alternatively, a miniature battery might be used. Today commercially available small batteries might have a lifetime spanning several months to years, depending on their use. In general any suitable powering method known to the skilled person for powering an implantable sensor can be selected.

The single-chip optical spectrometric sensor, together with power unit and wireless data-transmission electronics are packaged by e.g. moulding these components in a e.g. PDMS or PMMA based biocompatible package. The fabrication of PDMS or PMMA based material and the moulding of are well described in literature and state-of-the-art technology.

After production of the packaged sensor, including spectrometric sensor, power unit and wireless unit, the packaged sensor is implanted in the body under test.

In some embodiments of the present invention, a sensor and corresponding monitoring system is provided as described above, implanted in non-living objects. The sensor may for example be used in connection with a bioreactor to monitor levels of substances, e.g. nutrients and/or cellular waste products to maximize growth. It can also be used to monitor industrial chemical processes and/or environmental processes.

While the invention has been illustrated and described in detail in the drawings and foregoing description, such illustration and description are to be considered illustrative or exemplary and not restrictive. The invention is not limited to the disclosed embodiments. For example, the present invention also relates to a corresponding method whereby radiation is received in the sensor and spectrally processed using a photonics integrated circuit. The method may comprise further method steps expressing the functionality of the different components described for the sensor above. The result of such a method may be a qualification of the presence or a quantification of the presence of a substance. The detection results do not necessarily include an evaluation of such detection results the method therefore not necessarily being a diagnostic method.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage.

The algorithms implemented in the sensor may be implemented as software or as hardware. The algorithm may be implemented as a computer program performing control steps for controlling the sensor. Such a computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A sensor configured to sense glucose, urea, creatinine, triglyceride, protein, cholesterol, ethanol, ketones, hormones or lactate, the sensor being implantable in the body of a living creature or an object and configured for sensing in tissue or bodily fluids, the sensor comprising:
    an integrated radiation source configured for coupling radiation generated by said source into a photonics integrated circuit, the integrated radiation source being for irradiating said tissue or bodily fluids having at least one of glucose, urea, creatinine, triglyceride, protein, cholesterol, ethanol, ketones, hormones or lactate in said tissue or bodily fluid,
    a photonics integrated circuit configured to spectrally process the radiation interacting with the glucose, urea, creatinine, triglyceride, protein, cholesterol, ethanol, ketones, hormones or lactate, wherein the photonics integrated circuit comprises at least an integrated optical waveguide, an optical demultiplexer and a detection element,
    said integrated optical waveguide being configured for receiving radiation from said integrated radiation source and to send the radiation to the demultiplexer,
    said optical demultiplexer being configured for spectrally processing the radiation, said integrated detection element being configured to detect different absorption or reflection bands of the glucose, urea, creatinine, triglyceride, protein, cholesterol, ethanol, ketones, hormones or lactate from the spectrally processed radiation to sense the glucose, urea, creatinine, triglyceride, protein, cholesterol, ethanol, ketones, hormones or lactate, wherein the radiation source and the photonics integrated circuit form an integrated spectrometer, and wherein said sensor is configured to be implantable in the body of a living creature or an object to sense glucose, urea, creatinine, triglyceride, protein, cholesterol, ethanol, ketones, hormones or lactate.

2. The sensor according to claim 1, wherein the sensor is waveguide based and configured for free space sensing.

3. The sensor according to claim 1, the sensor comprising a measurement region from which the radiation is captured, wherein the photonics integrated circuit and measurement region are spatially configured to allow for substance-sampling free measurements.

4. The sensor according to claim 1, wherein the photonics integrated circuit and measurement region are sized so as to allow for time-dependent substance measurements based on spontaneous displacement of the substance in the body.

5. The sensor according to claim 1, wherein the measurement region is an open-space measurement region so that it is not enclosed by sensor walls.

6. The sensor according to claim 1, wherein the integrated detecting element is a detecting element monolithically integrated with the photonics integrated circuit or heterogeneously integrated with the photonics integrated circuit or hybridly integrated with the photonics integrated circuit.

7. The sensor according to claim 1, wherein the radiation source is a radiation source monolithically integrated with the photonics integrated circuit or heterogeneously integrated with the photonics integrated circuit or hybridly integrated with the photonics integrated circuit.

8. The sensor according to claim 1, wherein the photonics integrated circuit is a silicon photonics integrated circuit.

9. The sensor according to claim 1, wherein the photonics integrated circuit based sensor is adapted for operating in at least a wavelength region of 1560 nm to 1850 nm and/or is adapted for operating in at least a wavelength region of 2080 nm to 2325 nm.

10. The sensor according to claim 1, wherein the sensor is adapted for performing said spectrally processing radiation prior to interaction of the radiation with the substance to be sensed or wherein the sensor is adapted for performing said spectrally processing radiation after interaction of the radiation with the substance.

11. The sensor according to claim 1, wherein the sensor has a sensor configuration such that a measurement region of the sensor is surrounded by components of the sensor.

12. The sensor according to claim 1, wherein a measurement region of the sensor lies substantially at one side of all components of the sensor.

13. The sensor according to claim 1, the sensor being configured for obtaining depth-related information regarding the sample.

14. The sensor according to claim 1, wherein the sensor is configured for optical coherence tomography.

15. The sensor according to claim 1, wherein the sensor is configured for spectrally resolved optical coherence tomography wherein the photonics integrated circuit comprises an interferometer and is adapted for processing obtained interference data in several different windows and/or wherein the sensor is configured for spatially resolved detection and for deriving said depth-resolved information regarding the sample based thereon.

16. The sensor according to claim 1, wherein the photonics integrated circuit is adapted for spatially resolved detection of scattered or reflected radiation and/or wherein the photonics integrated circuit comprises a plurality of cascading wavelength multiplexers for increasing a number of channels for spectrally processing radiation and/or wherein the photonics integrated circuit comprises a plurality of tunable filters for increasing a number of channels for spectrally processing radiation.

17. The sensor according to claim 1, wherein frequency or time-domain multiplexing is used for increasing a number of channels for spectrally processing radiation and/or wherein a Vernier-shifted spectral response is used for increasing a number of channels for spectrally processing radiation.

18. The sensor according to claim 1, the sensor comprising an electronics component stacked with the sensing element and radiation source, wherein the connection between sensing element and radiation source on the one hand and the electronics on the other hand is made by through silicon vias.

19. The sensor according to claim 1, the sensor being a glucose sensor or the sensor being a urea sensor or the sensor being an optical coherence tomography imager or the sensor being implantable in a bioreactor.

20. A continuous monitoring system comprising an implantable sensor according to claim 1, and a readout system for wirelessly receiving data sensed by the sensor.

* * * * *